(12) United States Patent
Jonas et al.

(10) Patent No.: US 7,285,614 B2
(45) Date of Patent: Oct. 23, 2007

(54) SUPERABSORBENT POLYMER WITH SLOW ABSORPTION TIMES

(75) Inventors: Gerd Jonas, Krefeld (DE); Klaus Pflueger, Krefeld (DE); Rüdiger Gerlach, Mülheim (DE)

(73) Assignee: Stockhausen, Inc., Greensboro, NC (US)

( * ) Notice: Subject to any disclaimer, the term of this patent is extended or adjusted under 35 U.S.C. 154(b) by 303 days.

(21) Appl. No.: 10/660,982

(22) Filed: Sep. 12, 2003

(65) Prior Publication Data

US 2005/0059762 A1 Mar. 17, 2005

(51) Int. Cl.
*C08F 20/06* (2006.01)
(52) U.S. Cl. .................. 526/317.1; 525/330.2
(58) Field of Classification Search ............. 526/317.1; 525/330.2
See application file for complete search history.

(56) References Cited

U.S. PATENT DOCUMENTS

| 5,032,628 A | 7/1991 | Choi et al. |
| 5,610,220 A | 3/1997 | Klimmek et al. |
| 5,760,080 A * | 6/1998 | Wada et al. ............... 524/559 |
| 5,856,410 A | 1/1999 | Carrico et al. |
| 5,994,440 A | 11/1999 | Staples et al. |
| 6,090,875 A | 7/2000 | Staples et al. |
| RE38,444 E | 2/2004 | Wada et al. |

FOREIGN PATENT DOCUMENTS

| EP | 0712659 A | 5/1996 |
| WO | WO94/15651 A1 | 7/1994 |
| WO | 98/52979 | * 11/1998 |
| WO | WO98/52979 A1 | 11/1998 |

OTHER PUBLICATIONS

International Search Report mailed on Feb. 10, 2005 in PCT/US2004/029808.
Written Opinion of the International Searching Authority mailed on Feb. 10, 2005 in PCT/US2004/029808.

* cited by examiner

*Primary Examiner*—Roberto Rabago
(74) *Attorney, Agent, or Firm*—Smith Moore LLP

(57) ABSTRACT

The invention relates to hydrophilic superabsorbent polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; and d) wherein the composition has a degree of neutralization of more than about 20%, and from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent; at a temperature of about 75° C. or less. Such hydrophilic superabsorbent polymers have an Absorption Time of about 5+10 $a^2$ minutes or greater, where a is the mean particle size of the superabsorbent material in millimeters, a capacity of about 15 g/g or greater, a Drop Penetration Value of about 2 seconds or less, and a floatability of 50% or less.

22 Claims, 3 Drawing Sheets

SUPERABSORBENT POLYMER WITH SLOW ABSORPTION TIMES

FIELD OF THE INVENTION

The invention relates to superabsorbent polymers which absorb water, aqueous liquids and blood wherein the superabsorbent polymers of the present invention have improved properties, in particular a slower absorption time while maintaining acceptable fluid retention properties. The present invention also relates to preparation of these superabsorbent polymers and their use as absorbents in hygiene articles and in industrial fields.

BACKGROUND OF THE INVENTION

Superabsorbent refers to a water-swellable, water-insoluble, organic or inorganic material capable of absorbing at least about 10 times its weight and up to about 30 times its weight in an aqueous solution containing 0.9 weight percent sodium chloride solution in water. A superabsorbent polymer is a crosslinked polymer which is capable of absorbing large amounts of aqueous liquids and body fluids, such as urine or blood, with swelling and the formation of hydrogels, and of retaining them under a certain pressure in accordance with the general definition of superabsorbent.

The superabsorbent polymers that are currently commercially available are crosslinked polyacrylic acids or crosslinked starch-acrylic acid graft polymers, in which some of the carboxyl groups are neutralized with sodium hydroxide solution or potassium hydroxide solution. As a result of these characteristic properties, these polymers are chiefly used for incorporation into sanitary articles, such as babies' diapers, incontinence products or sanitary towels.

For fit, comfort and aesthetic reasons and from environmental aspects, there is an increasing trend to make sanitary articles smaller and thinner. This is being accomplished by reducing the content of the high volume fluff fiber of these articles. To ensure a constant total retention capacity of body fluids in the sanitary articles, more superabsorbent polymer content is being used in these sanitary articles. As a result of this, superabsorbent polymers must have increased permeability characteristics while retaining other characteristics such as adequate absorption and retention.

In particular, gel blocking is a well-known problem that may be associated with the use of superabsorbent polymers in absorbent articles such as diapers. Gel blocking occurs when rapid expansion of the superabsorbent polymer particles around the point of entry of body fluid into an absorbent article causes a closing of the interstitial spaces and pores in the SAP-fluff matrix. Since the transport of liquid by diffusion through swollen hydrogel is much slower than transport through the interstitial spaces, a sealing effect occurs in the area of fluid entry. This effect is referred to as gel blocking.

Transportation of liquid through swollen superabsorbent polymer particles themselves follows the laws of diffusion and is a very slow process which plays no role in the distribution of the liquid in the use situation of the sanitary article. In superabsorbent polymers, which cannot maintain an open bed structure to effect capillary transportation because of a lack of gel stability, the separation of the particles from one another has been ensured by embedding the superabsorbent polymer into a fiber matrix.

In diaper constructions, for what is called the next generation, there is less fiber material, or potentially none at all, in the absorber layer to assist in transportation of the liquid or maintenance of an open, fluid permeable structure. The superabsorbent polymer of these next generation diaper constructions must have a sufficiently high stability in the swollen state, generally called gel strength, so the swollen gel has a sufficient amount of capillary spaces through which liquid can be transported.

To obtain a superabsorbent polymer with high gel strength, the degree of crosslinking of the polymer may be increased, which necessarily results in a reduction in the swellability and the retention capacity. To achieve the increased permeabilities needed in extremely thin, next generation articles with low fiber content, current art has taught to increase the amount of covalent crosslinking to such high levels that the absorption and retention values of the superabsorbent polymers are reduced to undesirably low levels.

It has been found that by making a superabsorbent with a slower swelling rate, fluid transport and permeability in thin, low fiber next generation articles can be maintained by avoiding the rapid expansion of the superabsorbent polymer particles around the point of entry of body fluid into an absorbent article which causes a closing of the interstitial spaces and pores in the SAP-fluff matrix, i.e. gel blocking. Gel blocking can thereby be avoided without relying on overcrosslinking the superabsorbent polymer to achieve permeability. Superabsorbent polymers with slow absorption rates known in the art achieve their reduced swelling rate by either a hydrophobic treatment or a coating that delays absorption. Hydrophobicity is undesirable as it reduces the wicking ability of the bulk polymer and can prevent wetting of the SAP. Slowly dissolving coatings, such as with gelatin, increase the viscosity of the fluid in an absorbent article as they dissolve and hinder fluid transport.

It is therefore an object of the present invention to provide an absorbing polymer composition that exhibits excellent properties such as capabilities of maintaining high liquid permeability, hydrophilicity and liquid retention even when the superabsorbent polymer is increased in percent by weight based on the absorbent structure, by limiting the absorption rate of the polymer without introducing hydrophobic nature or the use of performance-hindering coatings.

SUMMARY OF THE INVENTION

The present invention is directed to a hydrophilic superabsorbent polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; and d) wherein the composition has a degree of neutralization of more than about 20%, and from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent; at a temperature of about 75° C. or less.

The present invention is also directed to a superabsorbent polymer having an Absorption Time of about $5+10\,a^2$ minutes or greater, where a is the mean particle size of the superabsorbent material in millimeters, a capacity as measured by the FAUZL test of about 15 g/g or greater, a Drop Penetration Value of about 2 seconds or less, and a floatability of about 50% or less.

The present invention is also directed to a superabsorbent polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; and d) wherein the unsaturated acid group containing monomers have a degree of neutralization of more than about 25%, and from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent; the superabsorbent polymer having an Absorption Time of about $5+10\ a^2$ minutes or greater, where a is the mean particle size of the superabsorbent material in millimeters, a capacity as measured by the FAUZL test of about 15 g/g or greater, a Drop Penetration Value of about 2 seconds or less, and a floatability of about 50% or less.

DESCRIPTION OF THE PREFERRED EMBODIMENTS

Figure 1:
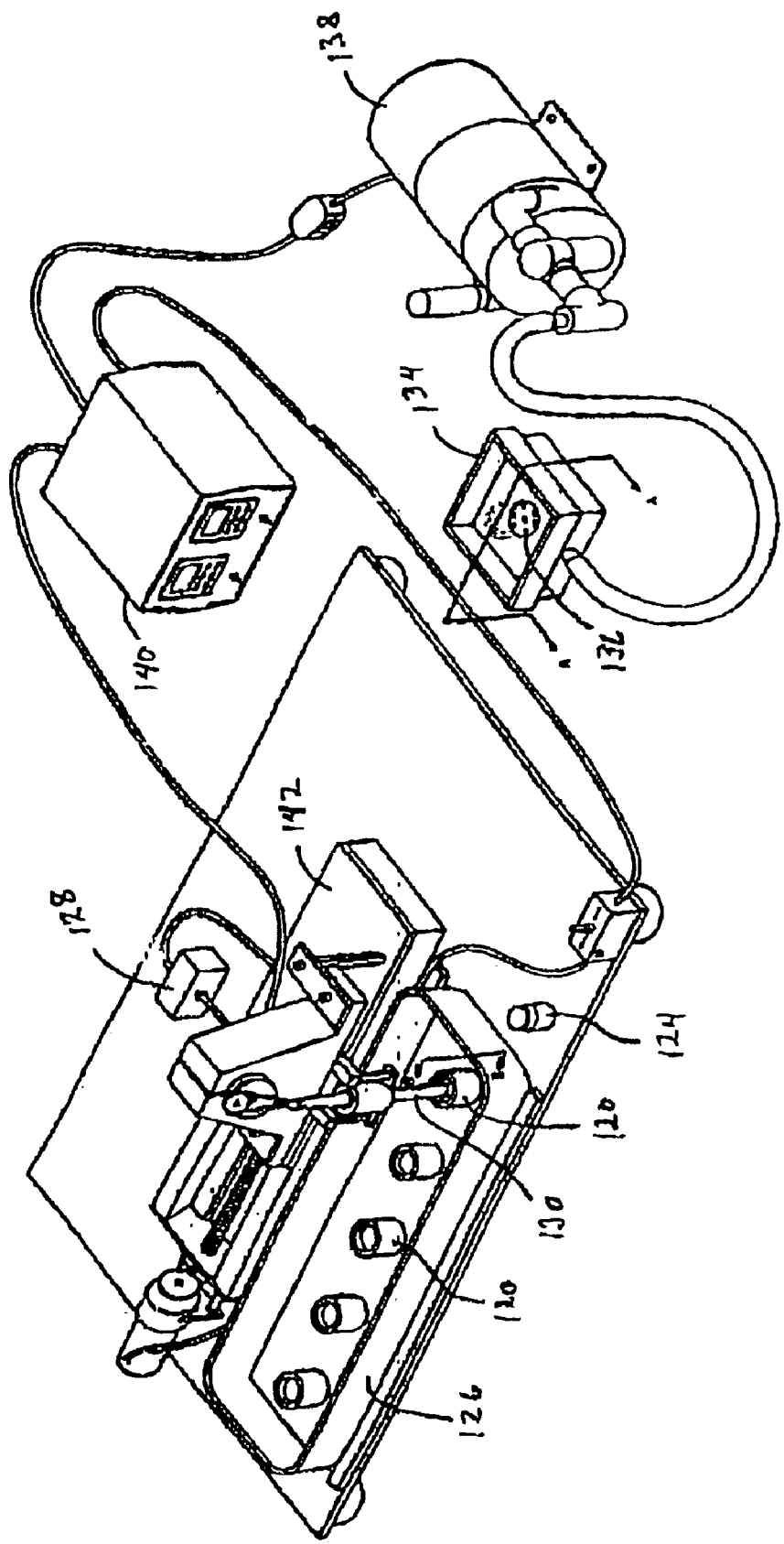
FIG. 1 is an illustration of equipment for determining the Flooded Absorbency Under Zero Load (FAUZL) value of a superabsorbent material.

A suitable superabsorbent polymer may be selected from natural, biodegradable, synthetic and modified natural polymers and materials. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and surface crosslinking.

One embodiment of the present invention is directed to a hydrophilic superabsorbent polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; and d) wherein the composition has a degree of neutralization of more than about 20%, and from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent; at a temperature of about 75° C. or less.

Another embodiment of the present invention, the superabsorbent polymer is a crosslinked polymer wherein the superabsorbent polymer the superabsorbent polymer has an absorption time of about $5+10\ a^2$ minutes or greater, where a is the mean particle size of the superabsorbent material in millimeters, a liquid capacity of about 15 g/g or greater, a drop penetration value of about 2 seconds or less, and a floatability of about 50% or less. Preferably, such superabsorbent polymers exhibit a FAUZL liquid capacity of about 20 g/g or more, and a gel bed permeability of $20 \times 10^{-9}\ cm^2$ or more. One preferred embodiment is a such superabsorbent polymer having a liquid capacity from about 25 to about 36 g/g; and a gel bed permeability from about 5 to $92 \times 10^{-9}\ cm^2$.

In another embodiment of the present invention, the superabsorbent polymer is a crosslinked polymer comprising a) from about 55 to about 99.9 wt. % of polymerizable unsaturated acid group containing monomers; b) from about 0.001 to about 5.0 wt. % of internal crosslinking agent; c) from about 0.001 to about 5.0 wt. % of surface crosslinking agent applied to the particle surface; and d) wherein the composition has a degree of neutralization of more than about 25%, and from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent; having an Absorption Time of about $5+10\ a^2$ minutes or greater, where a is the mean particle size of the superabsorbent polymer in millimeters, a capacity as measured by the FAUZL test of about 15 g/g or greater, a Drop Penetration Value of about 2 seconds or less, and a floatability of about 50% or less.

The superabsorbent polymer of the present invention is obtained by the initial polymerization of from about 55 to about 99.9 wt. % of polymerizable unsaturated acid group containing monomers. Suitable monomers include those containing carboxyl groups, such as acrylic acid, methacrylic acid or 2-acrylamido-2-methylpropanesulfonic acid, or mixtures of these monomers are preferred here. It is preferable for at least about 50-weight. %, and more preferably at least about 75 wt. % of the acid groups to be carboxyl groups. The acid groups are neutralized to the extent of at least about 25 mol %, preferably 25 mole % to 80 mole %, that is the acid groups are present in salt form. It is preferred to obtain polymers obtained by polymerization of acrylic acid or methacrylic acid, the carboxyl groups of which are neutralized to the extent of 50-80 mol %, in the presence of internal crosslinking agents.

The present invention is directed to a superabsorbent polymer that has been neutralized by a 2 step process in which from about 20 mole % to about 75 mole % of the unsaturated acid group containing monomers are neutralized with a first neutralizing agent, and from about 5 mole % to about 40 mole % of the unsaturated acid group containing monomers are neutralized with a second neutralizing agent such that the total neutralization is at least about 25 mole %, preferably to the extent of 50-80 mole %. In the present invention, neutralization is done at a temperature of about 75° C. or less; preferable at about 50° C. or less.

The first neutralization agents are monovalent hydroxides, ammonia, carbonates, bicarbonates or other standard neutralizing agents known in the art, excluding multivalent metal hydroxides. The first neutralization agent may also be a mixture of the above agents. Monovalent metal hydroxides such as sodium hydroxide or potassium hydroxide, and carbonates such as sodium carbonate or magnesium carbonate are preferred. The second neutralization agents are multivalent metal hydroxides such as calcium hydroxide and magnesium hydroxide. The first and second neutralization agents may be added consecutively or simultaneously to the monomer solution. Most preferably the first neutralization is sodium hydroxide and the second neutralization agent is calcium hydroxide or magnesium hydroxide. It is also preferred that at least 25%, more preferably at least 40%, of the neutralization be accomplished by the first neutralization agent.

Further monomers, which can be used for the preparation of the absorbent polymers according to the invention, are 0-40 wt. % of ethylenically unsaturated monomers which can be copolymerized with a), such as e.g. acrylamide, methacrylamide, hydroxyethyl acrylate, dimethylaminoalkyl (meth)-acrylate, ethoxylated (meth)-acrylates, dimethylaminopropylacrylamide or acrylamidopropyltrimethylammonium chloride. More than 40 wt. % of these monomers can impair the swellability of the polymers.

The internal crosslinking agent has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers such as multivalent metal salts may also be employed. Mixtures of the crosslinking agents mentioned can also be employed. The content of the internal crosslinking agents is from about 0.01 to about 5 wt. %, and preferably from about 0.1 to about 3.0 wt. %, based on the total amount of the polymerizable unsaturated acid group containing monomers.

The usual initiators, such as e.g. azo or peroxo compounds, redox systems or UV initiators, (sensitizers), and/or radiation are used for initiation of the free-radical polymerization.

The absorbent polymers are surface crosslinked after polymerization. Surface crosslinking is any process that increases the crosslink density of the polymer matrix in the vicinity of the superabsorbent particle surface with respect to the crosslinking density of the particle interior. The absorbent polymers are typically surface crosslinked by the addition of a surface crosslinking agent. Preferred surface crosslinking agents include chemicals with one or more functional groups, which are reactive towards pendant groups of the polymer chains, typically the acid groups. The content of the surface crosslinking agents is from about 0.01 to about 5 wt. %, and preferably from about 0.1 to about 3.0 wt. %, based on the weight of the dry polymer. A heating step is preferred after addition of the surface crosslinking agent.

Generally the present invention includes coating the particulate superabsorbent polymer with an alkylene carbonate followed by heating to effect surface crosslinking to improve the surface crosslinking density and the gel strength characteristics. More specifically a surface crosslinking agent is coated onto the particulate by mixing the polymer with an aqueous alcoholic solution of the alkylene carbonate surface cross linking agent. The amount of alcohol is determined by the solubility of the alkylene carbonate and is kept as low as possible for technical reasons, for instance protection against explosions. Suitable alcohols are methanol, ethanol, butanol, or butyl glycol as well as mixtures of these alcohols. The preferred solvent is water, which typically is used in an amount of 0.3 to 5.0% by weight, relative to particulate superabsorbent polymer. In some instances, the alkylene carbonate surface cross linking agent is dissolved in water, without any alcohol. It is also possible to apply the alkylene carbonate surface cross linking agent from a powder mixture, for example, with an inorganic carrier material, such as $SiO_2$, or in the vapor state by sublimation of the alkylene carbonate.

To achieve the desired surface cross linking properties, the alkylene carbonate has to be distributed evenly on the particulate superabsorbent polymer. For this purpose, mixing is effected in suitable mixers, such as fluidized bed mixers, paddle mixers, milling rolls, or twin-worm mixers. It is also possible to carry out the coating of the particular superabsorbent polymer during one of the process steps in the production of the particulate superabsorbent polymer. A particularly suitable process for this purpose is the inverse suspension polymerization process.

The thermal treatment, which follows the coating treatment, is carried out as follows. In general, the thermal treatment is at a temperature between 100 and 300° C. However, if the preferred alkylene carbonates are used, then the thermal treatment is at a temperature between 150 and 250° C. The treatment temperature depends on the dwell time and the kind of alkylene carbonate. At a temperature of 150° C., the thermal treatment is carried out for one hour or longer. On the other hand, at a temperature of 250° C., a few minutes, e.g., 0.5 to 5 minutes, are sufficient to achieve the desired surface cross linking properties. The thermal treatment may be carried out in conventional dryers, ovens, fluid bed driers, twin screw reactors and the like.

While particles are then used by way of example of the physical form of superabsorbent polymers, the invention is not limited to this form and is applicable to other forms such as fibers, foams, films, beads, rods and the like.

The absorbent polymers according to the invention can comprise include from 0 to about 5 wt % of a multivalent metal salt, based on the weight of the mixture, on the surface of the polymer. The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred and sulfates being the most preferred. Aluminium sulfate is the most preferred multivalent metal salt and is readily commercially available. The preferred form of aluminum sulfate is hydrated aluminum sulfate, preferably aluminum sulfate having from 12 to 14 waters of hydration. Mixtures of multivalent metal salts can be employed.

The polymer and multivalent metal salt suitably are mixed by dry blending, or preferably in solution, using means well known to those skilled in the art. Aqueous solutions are preferred. With dry blending, a binder may be employed in an amount which sufficient to ensure that a substantially uniform mixture of the salt and the superabsorbent polymer is maintained. The binder may be water or a nonvolatile organic compound having a boiling point of at least 150° C. Examples of binders include water, polyols such as propylene glycol, glycerin and poly(ethylene glycol).

The absorbent polymers according to the invention can comprise include up to about 0.01 to about 5 wt % of water-insoluble, inorganic powder. Examples of insoluble, inorganic powders include silicon dioxide, silicic acid, silicates, titanium dioxide, aluminium oxide, magnesium oxide, zinc oxide, talc, calcium phosphate, clays, diatomaceous earth, zeolites, bentonite, kaolin, hydrotalcite, activated clays, etc. The insoluble inorganic powder additive may be a single compound or a mixture of compounds selected from the above list. Of all these examples, microscopic noncrystal silicon dioxide or aluminum oxide preferred. Further, a preferred particle diameter of the inorganic powder is 1,000 µm or smaller, and more preferably 100 µm or smaller.

The superabsorbent polymer according to the invention may also include the addition of from 0 to about 5 wt % of a surfactant to the polymer particle surface. It is preferred that these be added immediately prior to, during or immediately after the surface crosslinking step.

Examples of such surfactants include anionic, non-ionic, cationic and amphoteric surface active agents, such as fatty acid salts, coco amines and amides and their salts, alkylsulfuric ester salts, alkylbenzene sulfonic acid salts, dialkyl sulfo-succinate, alkyl phosphate salt, and polyoxyethylene alkyl sulfate salt; polyoxyethylene alkyl ether, polyoxyethylene alkyl phenol ether, polyoxyethylene fatty acid ester, sorbitan fatty acid ester, polyoxy sorbitan fatty acid ester, polyoxyethylene alkylamine, fatty acid esters, and oxyethylene-oxypropylene block polymer; alkyl amine salts, quaternary ammonium salts; and lauryl dimethylamine oxide. However, it is not necessary to restrict the surfactant to those mentioned above. Such surfactants may be used individually, or in combination.

The superabsorbent polymers may also include from 0 to about 30 wt. % of water-soluble polymers, such as partly or completely hydrolysed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt. %, preferably 0-5 wt. %, based on the total amount of components a) to d). The water-soluble polymers, preferably synthetic polymers, such as polyvinyl alcohol, can also serve as a graft base for the monomers to be polymerized.

It is sometimes desirable to employ surface additives that perform several roles during surface modifications. For example, a single additive may be a surfactant, viscosity modifier and react to crosslink polymer chains.

The superabsorbent polymers may also include from 0 to about 2.0 wt % of dedusting agents, such as hydrophilic and hydrophobic dedusting agents such as those described in U.S. Pat. Nos. 6,090,875 and 5,994,440 may also be employed in the process of the invention.

Further additives of the superabsorbent polymers according to the invention may optionally be employed, such as odor-binding substances, such as cyclodextrins, zeolites, inorganic or organic salts and similar materials; anti-caking additives, flow modification agents and the like.

The polymers according to the invention are preferably prepared by two methods. The polymers can be prepared continuously or discontinuously in a large-scale industrial manner by the abovementioned known process, the after-crosslinking according to the invention being carried out accordingly.

According to the first method, the partly neutralized monomer, preferably acrylic acid, is converted into a gel by free-radical polymerization in aqueous solution in the presence of crosslinking agents and optionally further components, and the gel is comminuted, dried, ground and sieved off to the desired particle size. This solution polymerization can be carried out continuously or discontinuously.

Inverse suspension and emulsion polymerization can also be used for preparation of the products according to the invention. According to these processes, an aqueous, partly neutralized solution of monomers, preferably acrylic acid, is dispersed in a hydrophobic, organic solvent with the aid of protective colloids and/or emulsifiers and the polymerization is started by free radical initiators. The internal crosslinking agents either are dissolved in the monomer solution and are metered in together with this, or are added separately and optionally during the polymerization. The addition of a water-soluble polymer d) as the graft base optionally takes place via the monomer solution or by direct introduction into the oily phase. The water is then removed azeotropically from the mixture and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

In one embodiment, the superabsorbent polymer is used in the form of discrete particles. Superabsorbent polymer particles can be of any suitable shape, for example, spiral or semi-spiral, cubic, rod-like, polyhedral etc. Particle shapes having a large greatest dimension/smallest dimension ratio, like needles, flakes or fibers are also contemplated for use herein. Conglomerates of particles of superabsorbent polymers may also be used.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

A solution of 28 wt % acrylic acid in water is neutralized with sodium hydroxide to a degree of 60 mole % and with calcium hydroxide a further 10 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 2

A solution of 28 wt % acrylic acid in water is neutralized with sodium hydroxide to a degree of 50 mole % and with calcium hydroxide a further 20 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 3

A solution of 28 wt % acrylic acid in water is neutralized with sodium hydroxide to a degree of 30 mole % and with calcium hydroxide a further 40 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 4

A solution of 28 wt % acrylic acid in water is neutralized with sodium hydroxide to a degree of 40 mole % and with magnesium hydroxide a further 30 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 5

A solution of 28 wt % acrylic acid in water is neutralized with sodium hydroxide to a degree of 30 mole % and with calcium hydroxide a further 40 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

The particles were further sieved to a particle size of 150 to 300 microns.

Example 6

A solution of 28 wt % acrylic acid in water is neutralized with sodium hydroxide to a degree of 55 mole % and with calcium hydroxide a further 15 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 7

A solution of 28 wt % acrylic acid in water is neutralized with sodium hydroxide to a degree of 50 mole % and with magnesium hydroxide a further 20 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Example 8

A solution of 28 wt % acrylic acid in water is neutralized with sodium hydroxide to a degree of 65 mole % and with calcium hydroxide a further 5 mole % under constant cooling to maintain a temperature less than 40° C. 0.24 wt % polyethyleneglycol (300) diacrylate and 0.3 wt % allyloxypolyethyleneglycol-acrylate are added to the partially neutralized acrylic acid solution. After cooling to 5° C. and stripping the oxygen with nitrogen, the mixture is polymerized with standard radical chain polymerization techniques by the addition of 10 ppm ascorbic acid, 100 ppm 2,2'-azobis-(2-amidinopropane)dihydrochloride, 70 ppm hydrogen peroxide and 300 ppm sodium persulfate.

After completion of the polymerization (about 30 minutes), the resulting gel-like block is cut into small pieces and extruded through a die with 10 mm holes. The gel particles are then dried at 150° C. for 120 minutes in a forced air oven, reversing the air flow orientation to the polymer 180° after 30 minutes. The dried polymer is milled with a Retsch pin grinder and sieved to a particle size of 150 to 850 microns.

The base polymer is then uniformly coated with 6.5 wt % of a solution containing 7.7 wt % ethylene carbonate, 30.8 wt % water and 61.5 wt % acetone. The coated polymer was then heated to 180° C. for 25 minutes.

Table 1 summarizes the material characteristics of these and other superabsorbent materials.

TABLE 1

| Example Number | Equilibrium FAUZL Capacity (g/g) | Mean particle size (mm) | Calculated $5 + 10a^2$ (min) | Calculated $7 + 10a^2$ (min) | Calculated $10 + 10a^2$ (min) | Measured Absorption Time (min) | Drop Penetration Value (sec) | Gel Bed Permeability ($\times 10^{-9}$ cm$^2$) | Floatability (%) |
|---|---|---|---|---|---|---|---|---|---|
| 1 | 30.5 | 0.50 | 7.5 | 9.5 | 12.5 | 12.5 | <1 | 22 | 0 |
| 2 | 29.5 | 0.46 | 7.1 | 9.1 | 12.1 | 47 | <1 | 36 | 0 |
| 3 | 25.0 | 0.42 | 6.8 | 8.8 | 11.8 | 96.5 | <1 | 14 | 0 |
| 4 | 34.8 | 0.73 | 10.3 | 12.3 | 15.3 | 32.5 | <1 | 5 | 0 |
| 5 | 25.5 | 0.23 | 5.5 | 7.5 | 10.5 | 79.4 | <1 | — | 0 |
| 6 | 31.0 | 0.47 | 7.2 | 9.2 | 12.2 | 30 | <1 | 45 | 0 |
| 7 | 29.3 | 0.43 | 6.8 | 8.8 | 11.8 | 8 | <1 | 18 | 0 |
| 8 | 36.0 | 0.47 | 7.2 | 9.2 | 12.2 | 8 | <1 | 92 | 0 |

Test Methods

The methods for performing the Saline Drop Penetration Test, the Gel Bed Permeability (GBP) test, the Floatability test, the Mean Particle Size test, and the Flooded Absorbency Under Zero Load (FAUZL) test. Unless otherwise stated, the test fluid used in all the test methods described below is an aqueous 0.9 weight percent sodium chloride solution, such as that available from Ricca Chemical Company (Arlington, Tex.). Unless otherwise stated, all tests were conducted at about 70 degrees Fahrenheit and between 10 and 60% relative humidity.

Saline Drop Penetration Test

This test was designed to evaluate the hydrophobicity of a SAP/fluff absorbent composite using saline drops. The SAP/fluff ratio is 50/50, with 500 gsm basis weight and 0.2 g/cc density. The development of hydrophobicity is accelerated by baking the sample in a sealed container at 150° C. for 120 minutes. A pipette is used to put 10 saline drops, each about 0.05 grams, on different parts of the sample, and the penetration time of each drop into the sample is measured. The penetration time for each drop is measured independently. The time for each drop is started when that drop contacts the composite. The longest individual penetration time among the 10 drops is recorded as the Drop Penetration Value.

Baking for 120 minutes at 150° C. is equivalent to at least several months of laboratory, aging at ambient condition.

Flooded Absorbency Under Zero Load (FAUZL)

This test is designed to measure the saline absorption rate of particulate superabsorbent polymer (SAP). The test measures, as a function of time, the amount of saline absorbed by 0.160 grams of dry superabsorbent polymer when it is confined within a 5.07 cm² area under a determined nominal pressure of 0.01 psi (0.069 kPa). From the resulting absorption versus time data, the Absorption Time, to reach 60% of the equilibrium absorption capacity is determined.

The test utilizes an electronic balance, accurate to 0.001 gram (200 gram minimum capacity); a cylinder group including: 1 inch (25.4 mm) inside diameter plastic cylinder 120 with a 100 mesh stainless steel screen affixed to the cylinder bottom; and a 4.4 gram plastic piston disk 122 with a 0.995 inch (25.27 mm) diameter. The piston disk diameter is 0.005 inch (0.13 mm) smaller than the inside diameter of the cylinder. See FIG. 2. Also, aqueous 0.9 weight percent sodium chloride solution; a saline basin 126; a timer 140 capable of reading 120 minutes at one second intervals; and weighing paper (see FIG. 1).

Figure 2:
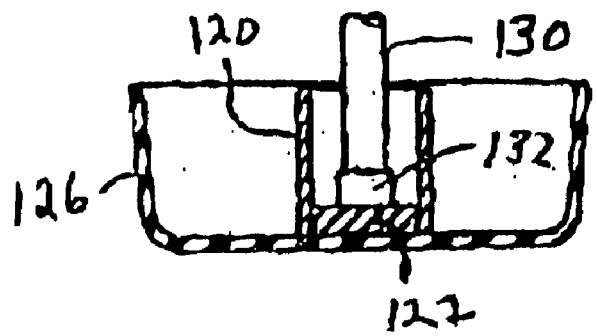
FIG. 2 is a cross-sectional view of a portion of the equipment for determining the Flooded Absorbency Under Zero Load (FAUZL) value shown in FIG. 1 and taken along section line B-B.
Figure 3:
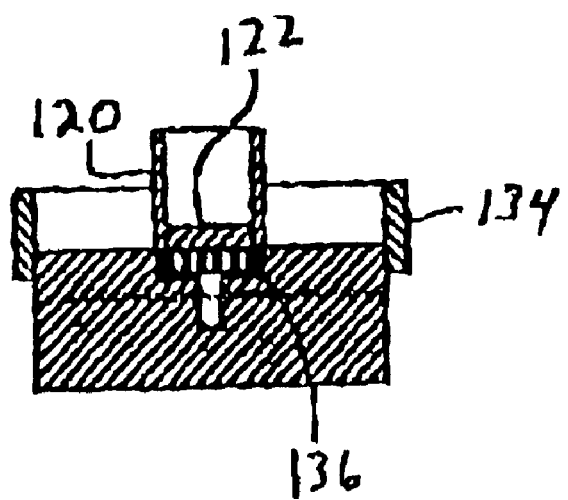
FIG. 3 is a cross-sectional view of a portion of the equipment for determining the Flooded Absorbency Under Zero Load (FAUZL) value shown in FIG. 1 and taken along section line A-A.

A tapping device is positioned above the sample, to provide a consistent tapping onto the supporting piston disk, as illustrated in FIGS. 2 and 3. This tapping dislodges any trapped air surrounding the superabsorbent and ensures that liquid wets the surface of the superabsorbent material. In this setup, a motor 128 rotates a shaft which drives a rod 130 along an up and down stroke. At the lower end of the rod is a rubber foot 132 which has a diameter of 13 mm, as illustrated in FIG. 2. The shaft stroke is 3 cm and it completes a full up and down stroke cycle every 0.7 seconds. The maximum pressure that the piston disk will apply to the SAP at impact is 0.16 psi (1.1 KPa).

With reference to FIG. 1, a fixture 134 has a vacuum port 136 that allows for the evacuation of interstitial liquid from the sample. The port accommodates the base of the cylinder group. When the cylinder group containing the sample is placed on the fixture, the free liquid is removed from between the superabsorbent particles. A suitable pump 138 applies a vacuum pressure to the sample of −13.5 psig (93.1 kPa) or less.

FIG. 1 shows the entire test setup. It should be noted that electronic timers 140 are suitably employed to control the duration of the tapping and vacuum devices. In this setup the tapping device also rests onto a slide 142 which would allow movement between multiple samples.

Procedure

1. Weigh out 0.160 grams (±0.001 grams) of superabsorbent onto the pre-tarred weighing paper. The particle size distribution is the "as received" particle size distribution of the superabsorbent material.

2. Slowly pour the superabsorbent material into the cylinder having the 100 mesh bottom. Avoid allowing the particles of SAP to contact the sides of the cylinder because particles may adhere. Gently tap the cylinder until the particles of the SAP are evenly distributed on the screen.

3. Place the plastic piston in the cylinder. Weigh this cylinder group and record the weight as the "cylinder group superabsorbent material amount."

4. Fill the saline basin to a 1 cm height with the blood bank saline.

5. Place the cylinder group in the saline basin, directly below the shaft of the tapping device and start the timer. Start and operate the tapping device to tap for an eight second cycle.

6. One minute after the cylinder is placed into the basin, remove the cylinder, stop the timer and place the cylinder onto the vacuum platform, as illustrated in FIG. 3. Apply the vacuum at −13.5 psig (93.1 kPa) for a 6 second period.

7. Weigh the cylinder group and record the weight.

8. Return the cylinder group to the basin below the tapping device and again start the timer. Note that the time between removing the cylinder group from the saline in step 6 to reintroducing the cylinder group to the saline in step 8 should not exceed 30 seconds. Repeat the initial sequence of soaking, removing, vacuuming, and weighing to gather and record data at cumulative soak times of 1, 5, 10, 15, 30, 45, 60, 75, 90, and 120 minutes.

9. Conduct the procedure described in steps 1-8 a total of three times.

Results and Analysis

Calculate the grams of saline absorbed per gram of superabsorbent polymer, and plot as a function of cumulative soak time.

Determine the final equilibrium absorption capacity of the SAP: if there is less than a 5% change in the average capacity (average of three tests) of the SAP obtained at 90 and 120 minutes then use the capacity at 120 minutes as the equilibrium capacity, FAUZL. If there is greater than a 5% change in the average capacity, then the sample testing will need to be repeated and will need to include an additional sampling at a cumulative soak time of 200 minutes. Use the capacity at 200 minutes as the equilibrium capacity, FAUZL, for this latter situation.

Determine the interpolated time to reach 60% of the equilibrium absorption capacity. This is done by calculating the capacity at 60% of the equilibrium value, then estimating the corresponding time to reach this capacity from the graph. The interpolated time to reach 60% capacity (by this procedure), is obtained by performing a linear interpolation with the data points that lay to either side of the estimated time.

Calculate the arithmetic average interpolated time to reach 60% of the equilibrium capacity (average of three tests). This average value is referred to as "Absorption Time."

Gel Bed Permeability (GBP)

Figure 4:
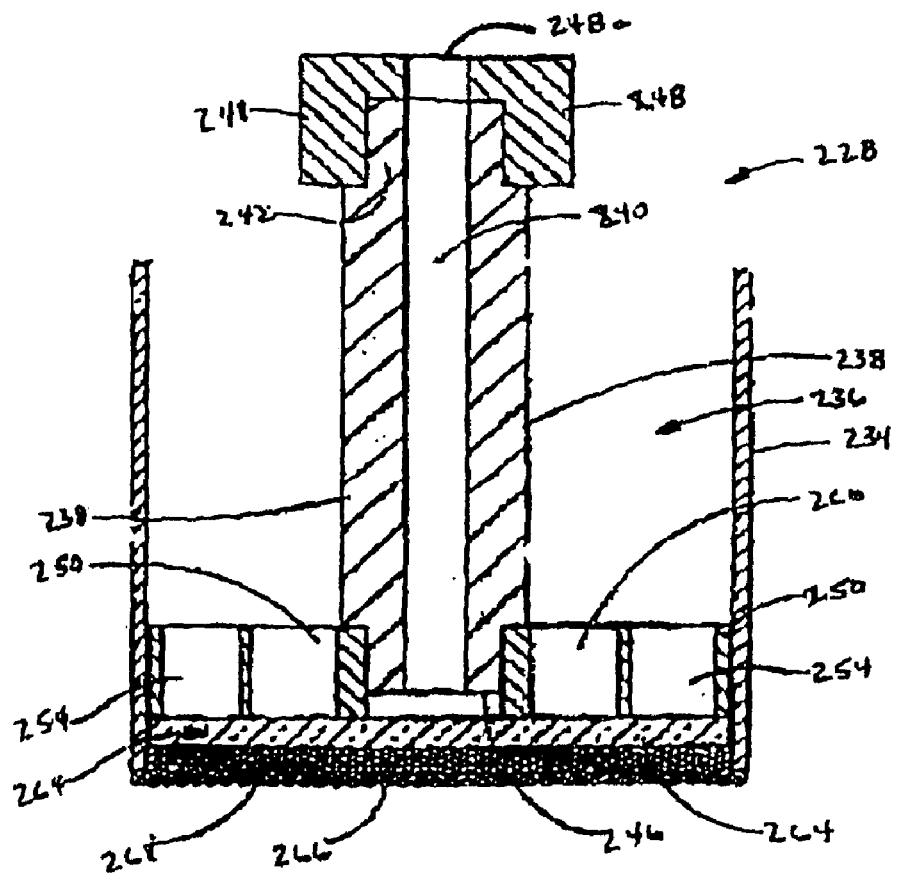
FIG. 4 is an illustration of equipment for determining the Gel Bed Permeability (GBP) value of a superabsorbent material.
Figure 5:
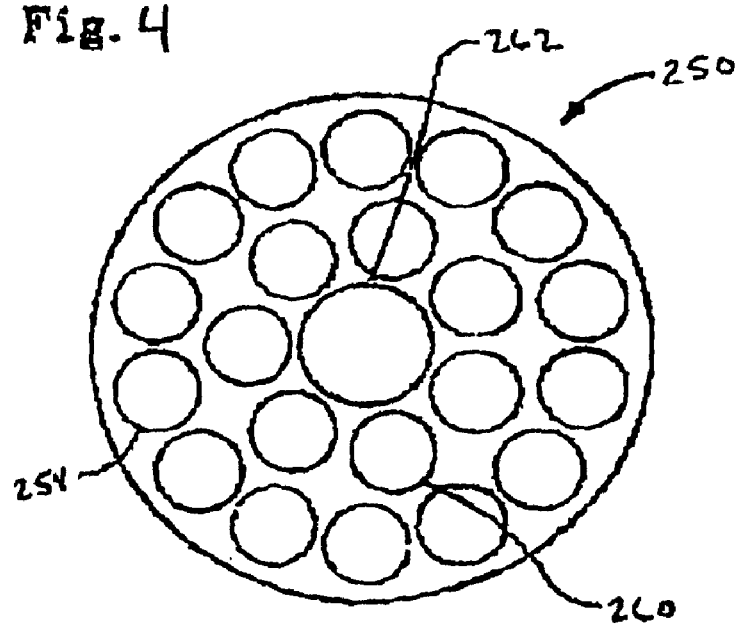
FIG. 5 is a cross-sectional view of the piston head taken along line 12-12 of FIG. 4.

A suitable piston/cylinder apparatus for performing the GBP test is shown in FIGS. 4 and 5. Referring to FIG. 4, apparatus 228 consists of a cylinder 234 and a piston generally indicated as 236. As shown in FIG. 4, piston 236 consists of a cylindrical LEXAN® shaft 238 having a concentric cylindrical hole 240 bored down the longitudinal axis of the shaft. Both ends of shaft 238 are machined to provide ends 242 and 246. A weight, indicated as 248, rests on end 242 and has a cylindrical hole 248a bored through the center thereof. Inserted on the other end 246 is a circular piston head 250. Piston head 250 is sized so as to vertically move inside cylinder 234. As shown in FIG. 5, piston head 250 is provided with inner and outer concentric rings containing seven and fourteen approximately 0.375 inch (0.95 cm) cylindrical holes, respectively, indicated generally by arrows 260 and 254. The holes in each of these concentric rings are bored from the top to bottom of piston head 250. Piston head 250 also has cylindrical hole 262 bored in the center thereof to receive end 246 of shaft 238.

Attached to the bottom end of cylinder 234 is a No. 400 mesh stainless steel cloth screen 266 that is biaxially stretched to tautness prior to attachment. Attached to the bottom end of piston head 250 is a No. 400 mesh stainless steel cloth screen 264 that is biaxially stretched to tautness prior to attachment. A sample of superabsorbent material indicated as 268 is supported on screen 266.

Cylinder 234 is bored from a transparent LEXAN® rod or equivalent and has an inner diameter of 6.00 cm (area=28.27 cm$^2$), a wall thickness of approximately 0.5 cm, and a height of approximately 5.0 cm. Piston head 250 is machined from a LEXAN® rod. It has a height of approximately 0.625 inches (1.59 cm) and a diameter sized such that it fits within cylinder 234 with minimum wall clearances, but still slides freely. Hole 262 in the center of the piston head 250 has a threaded 0.625 inch (1.59 cm) opening (18 threads/inch) for end 246 of shaft 238. Shaft 238 is machined from a LEXAN® rod and has an outer diameter of 0.875 inches (2.22 cm) and an inner diameter of 0.250 inches (0.64 cm). End 146 is approximately 0.5 inches (1.27 cm) long and is threaded to match hole 262 in piston head 250. End 242 is approximately 1 inch (2.54 cm) long and 0.623 inches (1.58 cm) in diameter, forming an annular shoulder to support the stainless steel weight 248. The annular stainless steel weight 248 has an inner diameter of 0.625 inches (1.59 cm), so that it slips onto end 242 of shaft 238 and rests on the annular shoulder formed therein. The combined weight of piston 236 and weight 248 equals approximately 596 g, which corresponds to a pressure of 0.30 psi (20,685 dynes/cm$^2$) for an area of 28.27 cm$^2$.

When solutions flow through the piston/cylinder apparatus, the cylinder 234 generally rests on a 16 mesh rigid stainless steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the gel bed. It is important to measure each cylinder empty and keep track of which piston and weight were used. The same piston and weight should be used for measurement when gel is swollen.

The superabsorbent layer used for GBP measurements is formed by swelling approximately 0.9 g of a superabsorbent material in the GBP cylinder apparatus (dry polymer should be spread evenly over the screen of the cylinder prior to swelling) with an aqueous 0.9 weight percent sodium chloride solution for a time period of about 60 minutes. The sample is taken from superabsorbent material which is prescreened through U.S. standard #30 mesh and retained on U.S. standard #50 mesh. The superabsorbent material, therefore, has a particle size of between 300 and 600 microns. The particles may be pre-screened by hand or automatically pre-screened with, for example, a Ro-Tap Mechanical Sieve Shaker Model B available from W. S. Tyler, Inc., Mentor, Ohio.

At the end of this period, the cylinder is removed from the fluid and the piston weight assembly is placed on the gel layer. The thickness of the swollen superabsorbent layer is determined by measuring from the bottom of the weight to the top of the cylinder with a micrometer. The value obtained when taking this measurement with the empty cylinder is subtracted from the value obtained after swelling the gel. The resulting value is the height of the gel bed H.

The GBP measurement is initiated by adding the NaCl solution to cylinder 234 until the solution attains a height of 4.0 cm above the bottom of superabsorbent layer 268. This solution height is maintained throughout the test. The quantity of fluid passing through superabsorbent layer 268 versus time is measured gravimetrically. Data points are collected every second for the first two minutes of the test and every two seconds for the remainder. When the data are plotted as quantity of fluid passing through the bed versus time, it becomes clear to one skilled in the art when a steady flow rate has been attained. Only data collected once the flow rate has become steady is used in the flow rate calculation. The flow rate, Q, through the superabsorbent layer 268, is determined in units of gm/sec by a linear least-square fit of fluid passing through the superabsorbent layer 268 (in grams) versus time (in seconds).

Permeability in cm$^2$ is obtained by the following equation:

$$K=[Q*H*Mu)]/[A*Rho*P]$$

K=Gel Bed Permeability (cm$^2$); Q=flow rate (g/sec);

H=height of gel bed (cm); Mu=liquid viscosity (poise);

A=cross-sectional area for liquid flow (cm$^2$); Rho=liquid density (g/cm$^3$); and P=hydrostatic pressure (dynes/cm$^2$) [normally 3923 dynes/cm$^2$].

Floatability

The floatability test is designed to measure the floatability of particulate superabsorbent polymers (SAP).

The test utilizes a 500 ml beaker, two small-tipped spatulas, tweezers, plastic vials having an inner diameter of about 2-3 cm and a height of about 3-4 cm, saline, a weight balance and a timer.

First, spread 0.10 g of 300-600 μm SAP in a plastic vial and drop saline (0.9% NaCl) to designed pre-saturation levels (as determined herein below), then cover the vial. Wait for equilibrium to be established (about 200 minutes). Then, use a small-tipped spatula to take SAP out of the vial and separate SAP on a particle by particle basis. Place about 300 ml of saline in the beaker. Gently drop a particle of SAP from about 1 cm height above the saline surface on the surface of the saline. Start the timer when the particle touches the saline surface. Wait 45 seconds and then record whether the particle of SAP floats or sinks. A particle is designated as sinking if the whole particle sinks completely below the surface of the saline. Repeat until 20 particles have been tested. Calculate the percentage of SAP particles that float. This equates to the "float percentage". Graph the float percentage as a function of saturation.

To prepare the pre-saturation level, use a small vial with a cover. "Saturation" is defined as: Saturation=(liquid weight/dry SAP weight) in g/g normalized to the equilibrium FAUZL absorption capacity of the superabsorbent (as defined above) in g/g. Weigh 0.1 g of SAP. Drop the SAP into the desired amount of saline to achieve the desired saturation level (liquid/solid g/g). Shake the container and let the saline mix with the SAP to form as homogeneous of a mixture as possible. Seal the container and wait to the equilibrium state (about 200 minutes). Then, start the floatability test.

Mean Particle Size Test Method

The particle size distribution of superabsorbent material is determined by placing a known weight of a sample in a Ro-Tap mechanical sieve shaker with U.S. standard sieves and shaking it for a specified period of time under defined conditions. Sample sections that are retained on each sieve are used to compute the mean particle size.

25±0.1 grams of superabsorbent is weighed and set aside for testing. The sieves are stacked on to the Ro-Tap in the following order from bottom to top: bottom pan, 325 mesh, 170 mesh, 50 mesh, 30 mesh, and 20 mesh. The superabsorbent sample weighed above is poured into the top sieve (#20) and then the sieve is covered. The Ro-Tap is allowed to run for 10 minutes and then stopped. The amount of superabsorbent retained on each pan is noted. The mass fraction of superabsorbent retained on each sieve, is referred to as $m_i$, and is computed by taking the ratio of the retained mass of superabsorbent to the total mass of superabsorbent. For the purpose of computing the mean particle size, it is assumed that all the particles retained on a particular sieve have a size $r_i$, equal to the average of the sieve above and sieve it is retained on. For example, superabsorbent retained on the 50 mesh screen would be inferred to all be 450 μm (average of 300 um corresponding to the 50 mesh and 600 um corresponding to the 30 mesh). Samples retained on the 20 mesh sieve are assumed to be 1000 μm size. Samples retained on the pan are assumed to be 22 um (average of 44 um corresponding to the 325 mesh and 0 um corresponding to the pan). The mean particle size is then computed as:

MeanParticleSize=$\Sigma m_i * r_i$

The examples described for the process according to the invention all show a very good overall performance, in particular in respect to the relationship of retention and permeability. Free-flowing coated powders that can easily be metered are obtained.

What is claimed:

1. A hydrophilic superabsorbent polymer composition comprising an absorbent polymer that is the reaction product of:
   a) from about 55 to about 99.9 wt. % based on the absorbent polymer of polymerizable unsaturated acid group containing monomers;
   b) a first neutralizing agent selected from monovalent hydroxides, monovalent carbonate, or monovalent bicarbonate salts, or mixtures thereof;
   c) a second neutralizing agent comprising a multivalent metal hydroxide;
   d) from about 0.001 to about 5.0 wt. % based on the weight of a) of internal crosslinking agent; and
   e) an initiator for initiation of free-radical polymerization;
   wherein the absorbent polymer has a degree of neutralization of more than about 25%, and from about 20 mole % to about 75 mole % of the unsaturated acid group containing monomers are neutralized with the first neutralizing agent, and from about 5 mole % to about 40 mole % of the unsaturated acid group containing monomers are neutralized with the second neutralizing agent, at a temperature of about 75° C. or less, and the absorbent polymer is formed into an absorbent polymer particle which is surface treated with from about 0.001 to about 5.0 wt. % of surface crosslinking agent applied to the polymer particle surface; and wherein the hydrophilic superabsorbent polymer composition has an absorption time of about 5+10 $a^2$ minutes or greater, where a is the mean particle size of the superabsorbent material in millimeters, a liquid capacity of about 15 g/g or greater, a drop penetration value of about 2 seconds or less, and a floatability of about 50% or less.

2. The hydrophilic superabsorbent polymer composition of claim 1 having a liquid capacity of about 20 g/g or greater.

3. The hydrophilic superabsorbent polymer composition of claim 1 having a liquid capacity of about 25 g/g or greater.

4. The hydrophilic superabsorbent polymer composition of claim 1 having an Absorption Time of about 7+10 $a^2$ minutes or greater.

5. The hydrophilic superabsorbent polymer composition of claim 1 having an Absorption Time of about 10+10 $a^2$ minutes or greater.

6. The hydrophilic superabsorbent polymer composition of claim 1 having a Gel Bed Permeability of about $20 \times 10^{-9}$ $cm^2$ or greater.

7. The hydrophilic superabsorbent polymer composition of claim 1 having a Gel Bed Permeability of about $50 \times 10^{-9}$ $cm^2$ or greater.

8. The hydrophilic superabsorbent polymer composition of claim 1 having a Gel Bed Permeability of about $80 \times 10^{-9}$ $cm^2$ or greater.

9. The hydrophilic superabsorbent polymer composition of claim 1 wherein the first neutralizing agent is sodium hydroxide, and the second neutralizing agent is selected from calcium hydroxide or magnesium hydroxide.

10. The hydrophilic superabsorbent polymer composition of claim 1 wherein at least 40% of the neutralization is accomplished by the first neutralizing agent.

11. The hydrophilic superabsorbent polymer composition of claim 1 wherein the first neutralizing agent comprises a monovalent metal hydroxide.

12. A water insoluble, cross-linked, partially neutralized, hydrophilic, superabsorbent polymer composition having a degree of neutralization of more than about 25%, wherein the hydrophilic superabsorbent polymer composition comprises an absorbent polymer that is the reaction product of polymerizable unsaturated acid group containing monomers, an internal crosslinking agent, and an initiator for initiation of free-radical polymerization; wherein from about 20 mole % to about 75 mole % of the unsaturated acid group containing monomers are neutralized with a first neutralizing agent selected from monovalent hydroxide, monovalent carbonate or bicarbonate salts, or mixtures thereof, and from about 5 mole % to about 40 mole % of the unsaturated acid group containing monomers are neutralized with a second neutralizing agent comprising a multivalent metal hydroxide; wherein the hydrophilic superabsorbent polymer composition has an absorption time of about 5+10 $a^2$ minutes or greater, where a is the mean particle size of the superabsorbent material in millimeters, a liquid capacity of about 15 g/g or greater, a drop penetration value of about 2 seconds or less, and a floatability of about 50% or less.

13. The water insoluble, cross-linked, partially neutralized, hydrophilic, superabsorbent polymer composition of claim 12 having a liquid capacity of about 20 g/g or greater.

14. The water insoluble, cross-linked, partially neutralized, hydrophilic, superabsorbent polymer composition of claim 12 having a liquid capacity of about 25 g/g or greater.

15. The water insoluble, cross-linked, partially neutralized, hydrophilic, superabsorbent polymer composition of claim 12 having an Absorption Time of about 7+10 $a^2$ minutes or greater.

16. The water insoluble, cross-linked, partially neutralized, hydrophilic, superabsorbent polymer composition of claim 12 having an Absorption Time of about 10+10 $a^2$ minutes or greater.

17. The water insoluble, cross-linked, partially neutralized, hydrophilic, superabsorbent polymer composition of claim 12 having a Gel Bed Permeability of about $20 \times 10^{-9}$ $cm^2$ or greater.

18. The water insoluble, cross-linked, partially neutralized, hydrophilic, superabsorbent polymer composition of claim 12 having a Gel Bed Permeability of about $50 \times 10^{-9}$ $cm^2$ or greater.

19. The water insoluble, cross-linked, partially neutralized, hydrophilic, superabsorbent polymer composition of claim 12 having a Gel Bed Permeability of about $80 \times 10^{-9}$ $cm^2$ or greater.

20. A hydrophilic superabsorbent polymer composition comprising an absorbent polymer that is the reaction product of:
- a) from about 55 to about 99.9 wt. % based on the absorbent polymer of polymerizable unsaturated acid group containing monomers;
- b) a first neutralizing agent selected from monovalent hydroxides, monovalent carbonate or bicarbonate salts, or mixtures thereof;
- c) a second neutralizing agent comprising a multivalent metal hydroxide;
- d) from about 0.001 to about 5.0 wt. % based on the weight of a) of internal crosslinking agent; and
- e) an initiator for initiation of free-radical polymerization;

wherein the absorbent polymer has a degree of neutralization of more than about 25%, and from about 20 mole % to about 75 mole % of the unsaturated acid group containing monomers are neutralized with the first neutralizing agent, and from about 5 mole % to about 40 mole % of the unsaturated acid group containing monomers are neutralized with the second neutralizing agent, and the absorbent polymer is formed into a absorbent polymer particle which is surface treated with from about 0.001 to about 5.0 wt. % of surface crosslinking agent applied to the particle surface.

21. The hydrophilic superabsorbent polymer composition of claim 20 wherein at least 40% of the neutralization is accomplished by the first neutralizing agent.

22. The hydrophilic superabsorbent polymer composition of claim 20 wherein the first neutralizing agent comprises a sodium hydroxide, and the second neutralizing agent is selected from calcium hydroxide or magnesium hydroxide.

* * * * *

UNITED STATES PATENT AND TRADEMARK OFFICE
CERTIFICATE OF CORRECTION

PATENT NO.        : 7,285,614 B2  
APPLICATION NO.   : 10/660982  
DATED             : October 23, 2007  
INVENTOR(S)       : Gerd Jonas, Klaus Pflueger and Rüdiger Gerlach Page 1 of 1

It is certified that error appears in the above-identified patent and that said Letters Patent is hereby corrected as shown below:

<u>Column 17</u>

Line 9, "300 um" should read -- 300 μm --

Line 10, "um corresponding" should read -- μm corresponding --

Line 12, "22 um" should read -- 22 μm --

Line 13, "um corresponding to the 325 mesh and 0 um corresponding" should read -- μm corresponding to the 325 mesh and 0 μm corresponding --

Signed and Sealed this

Seventeenth Day of June, 2008

JON W. DUDAS  
*Director of the United States Patent and Trademark Office*